(12) United States Patent
Olbert et al.

(10) Patent No.: US 7,268,254 B2
(45) Date of Patent: Sep. 11, 2007

(54) PREPARATION OF (METH)ACROLEIN AND/OR (METH)ACRYLIC ACID BY HETEROGENEOUSLY CATALYZED PARTIAL OXIDATION OF C3 AND/OR C4 PRECURSOR COMPOUNDS IN A REACTOR HAVING THERMOPLATE MODULES

(75) Inventors: Gerhard Olbert, Dossenheim (DE); Claus Hechler, Ludwigshafen, DE (US)

(73) Assignee: BASF Aktiengesellschaft, Ludwigshafen (DE)

( * ) Notice: Subject to any disclaimer, the term of this patent is extended or adjusted under 35 U.S.C. 154(b) by 440 days.

(21) Appl. No.: 10/889,081

(22) Filed: Jul. 13, 2004

(65) Prior Publication Data

US 2005/0020851 A1    Jan. 27, 2005

Related U.S. Application Data

(60) Provisional application No. 60/489,510, filed on Jul. 24, 2003.

(30) Foreign Application Priority Data

Jul. 24, 2003    (DE) ................................. 103 33 867
Apr. 7, 2004    (DE) ........................ 10 2004 017 150

(51) Int. Cl.
C07C 57/02    (2006.01)
C07C 45/00    (2006.01)

(52) U.S. Cl. ........................ 562/598; 568/475; 568/476
(58) Field of Classification Search ..................... None
See application file for complete search history.

(56) References Cited

FOREIGN PATENT DOCUMENTS

| DE | 197 54 185 | 2/1999 |
|---|---|---|
| DE | 198 48 208 | 4/2000 |
| DE | 199 52 964 | 5/2001 |
| DE | 19952964 | * 10/2001 |
| WO | WO 01/85331 | 11/2001 |

* cited by examiner

*Primary Examiner*—Paul A. Zucker
(74) *Attorney, Agent, or Firm*—Oblon, Spivak, McClelland, Maier & Neustadt, P.C.

(57) ABSTRACT

A process is proposed for partial oxidation oxidation in the gas phase of C3 and/or C4 precursor compounds to (meth) acrolein and/or (meth)acrylic acid in the presence of a heterogeneous particulate catalyst in a reactor having one or more cuboidal thermoplate modules (1) which are each formed from two or more rectangular thermoplates (2) arranged parallel to each other while in each case leaving a gap (3) which can be filled with the heterogeneous particulate catalyst and is flowed through by the fluid reaction mixture; the heat of reaction being absorbed by a heat carrier which flows through the thermoplates (2) and thus at least partly evaporating, and also having a predominantly cylindrical shell (4, 15, 16) which releases the pressure at the thermoplate modules, completely surrounds them and comprises a cylinder jacket (4) and hoods (15, 16) which seal it at both ends and whose longitudinal axis is aligned parallel to the plane of the thermoplates (2), and also having one or more sealing elements (7, 23) which are arranged in such a way that the fluid reaction mixture, apart from flowing through the reactor interior spaces bounded by the hoods (15, 16), only flows through the gap (3).

30 Claims, 10 Drawing Sheets

PREPARATION OF (METH)ACROLEIN AND/OR (METH)ACRYLIC ACID BY HETEROGENEOUSLY CATALYZED PARTIAL OXIDATION OF C3 AND/OR C4 PRECURSOR COMPOUNDS IN A REACTOR HAVING THERMOPLATE MODULES

The invention relates to a process for preparing (meth) acrolein and/or (meth)acrylic acid by partial oxidation in the gas phase of C3 and/or C4 precursor compounds in the presence of a heterogeneous particulate catalyst in 1, 2 or 3 reaction stages in a reactor having thermoplate modules.

As is well known, the abbreviated notation (meth)acrolein denotes acrolein and/or methacrolein. In a similar manner, the abbreviated notation (meth)acrylic acid is used for acrylic acid and/or methacrylic acid.

As is well known, the partial oxidation of C3 and/or C4 precursor compounds, such as propylene, propane, isobutene, isobutane, isobutanol, the methyl ether of i-butanol, acrolein or methacrolein (i.e. in particular of hydrocarbons containing 3 or 4 carbon atoms) in the gas phase is carried out in the presence of heterogeneous particulate catalysts. These reactions are strongly exothermic and have hitherto been carried out on the industrial scale predominantly in tube bundle reactors having catalyst tubes, into which the heterogeneous particulate catalyst is introduced and through which the fluid reaction mixture is passed, and the heat of reaction which is released is removed indirectly via a heat carrier which circulates in the intermediate space between the catalyst tubes. The heat carrier used is frequently a salt melt.

Such processes are described, for example, in DE-A 19 62 431, DE-A 29 43 707 or DE-A 199 52 964.

The reaction can be carried out starting from an alkane in one reaction stage to the acid, or in a first stage to the aldehyde and in a second stage to the acid. An alternative procedure may go in a first of three stages from the alkane to the olefin, in a second from the olefin to the aldehyde and in a third from the aldehyde to the acid. Starting from the olefin, the oxidation may in turn be effected in two stages, first to the aldehyde and then to the acid, or else in one stage from the olefin to the acid. The acid may also be prepared in one stage starting from the particular aldehyde. In this context, the aldehyde is (meth)acrolein and the acid is (meth)acrylic acid.

As an alternative, it is also possible to remove the heat of reaction via a heat carrier which is passed through plate-type heat transferors. The terms heat exchanger plates, heat transferor plates and thermoplates are used substantially synonymously for plate-type heat exchangers.

Heat transferor plates are defined predominantly as sheetlike structures which have an interior provided with inlet and outlet lines and having a low thickness in comparison to the surface area. They are generally produced from metal sheets, frequently from steel sheets. However, depending on the application case, in particular the properties of the reaction medium and of the heat carrier, special, in particular corrosion-resistant, or else coated materials may be used. The inlet and outlet devices for the heat carriers are generally arranged at opposite ends of the heater exchange plates. The heat carriers used are frequently water, or else Diphyl® (mixture of from 70 to 75% by weight of diphenyl ether and from 25 to 30% by weight of diphenyl), which sometimes also evaporate in a boiling procedure; it is also possible to use other organic heat carriers having a low vapor pressure and also ionic liquids.

The use of ionic liquids as heat carriers is described in the German patent application 103 16 418.9 which was unpublished at the priority date of the present application. Preference is given to ionic liquids which contain a sulfate, phosphate, borate or silicate anion. Also particularly suitable are ionic liquids which contain a monovalent metal cation, in particular an alkali metal cation, and also a further cation, in particular an imidazolium cation. Also advantageous are ionic liquids which contain an imidazolium, pyridinium or phosphonium cation as the cation.

The term thermoplates is used in particular for heat transferor plates whose single, usually two, metal plates are joined together by point and/or roll welds and are frequently shaped using hydraulic pressure plastically to form pockets.

In the present context, the term thermoplates is used in the sense of the above definition.

Reactors for carrying out partial oxidations using thermoplates are known, for example, from DE-A 199 52 964. The arrangement is described of a catalyst for carrying out partial oxidations in a bed around heat transferor plates in a reactor. The reaction mixture is fed at one reactor end to the reactor interior between the heat transferor plates and removed at the opposite end and thus flows through the interior between the heat transferor plates. As a result, there is constant transverse mixing of the reaction mixture with the consequence of high homogeneity thereof, and, for a predefined conversion, a substantially better selectivity is achieved compared to carrying out the reaction in a tube bundle reactor.

DE-C 197 54 185 describes a further reactor having indirect heat removal via a cooling medium which flows through the heat transferor plates, the heat transferor plates being designed as thermal plates which consist of at least two steel plates which are joined together at predefined points to form flow channels.

An advantageous development thereof is described in DE-A 198 48 208, according to which heat transferor plates which are configured as thermal plates flowed through by a cooling medium are combined to plate assemblies having, for example, rectangular or square cross section, and the plate assemblies have a casing. The encased plate assembly needs no adaptation on the circumferential side and is consequently used with predefined spacings to the interior wall of the cylindrical reactor vessel. The free surfaces between the plate heat transferor or its casing and the vessel interior wall are covered in the upper and lower regions of the casing with guide plates, in order to prevent the reaction medium from bypassing the chambers filled with catalyst.

A further reactor having devices for removing the heat of reaction which are in the form of plate heat transferors is described in WO-A01/85331. The reactor of predominantly cylindrical shape contains a continuous catalyst bed, into which a plate heat transferor is embedded.

(Meth)acrolein and/or (meth)acrylic acid are prepared on the industrial scale by partial oxidation of C3 and/or C4 precursor compounds in the presence of a suitable heterogeneous particulate catalyst. In order to bring about flow of the process gas through the catalyst bed, a pressure drop is required between gas inlet and outlet. This pressure drop may be imposed, for example, by an elevated pressure at the inlet or else by a reduced pressure at the outlet or a combination of these two measures. In the case of the catalysts used industrially which enable economic product preparation, a typical pressure drop over the catalyst bed is from 0.2 to 0.6 bar and, relative to the environment, the pressure differential may quite possibly be 1 bar and in some cases more.

In tubular reactors, this pressure differential relative to the environment is borne by a cylindrical configuration of the pressurized walls. Extended experiments on reactors having thermoplates have shown that problems occur in particular by deformation as a consequence of high stress on one side of the thermoplates at too high a pressure differential between the reaction mixture and the external environment, and also mechanical stability problems as a result of deformation under high thermal stress. These problems can occur when the reaction mixture is under elevated pressure, but also when the reaction is operated at reduced pressure.

It is an object of the present invention to provide a reactor which has removal of the heat of reaction via a heat carrier which flows through thermoplates, and can be operated for the industrial scale preparation of (meth)acrolein and/or (meth)acrylic acid by partial oxidation of C3/C4 precursor compounds in the presence of a heterogeneous particulate catalyst, in an economic and trouble-free manner, in particular avoiding the problems illustrated above. The invention should ensure the geometric stability of the thermoplate modules, particularly of the gaps designated to accommodate the catalyst, especially when carrying out the reaction to give (meth)acrolein and/or (meth)acrylic acid.

We have found that this object is achieved by a process for partial oxidation in the gas phase of C3 and/or C4 precursor compounds to (meth)acrolein and/or (meth)acrylic acid in the presence of a heterogeneous particulate catalyst in a reactor having one or more cuboidal thermoplate modules which are each formed from two or more rectangular thermoplates arranged parallel to each other while in each case leaving a gap which can be filled with the heterogeneous particulate catalyst and is flowed through by the fluid reaction mixture, the heat of reaction being absorbed by a heat carrier which flows through the thermoplates and thus at least partly evaporating, and also having a predominantly cylindrical shell which releases the pressure at the thermoplate modules, completely surrounds them and comprises a cylinder jacket and hoods which seal it at both ends and whose longitudinal axis is aligned parallel to the plane of the thermoplates, and also having one or more sealing elements which are arranged in such a way that the fluid reaction mixture, apart from flowing through the reactor interior spaces bounded by the hoods, only flows through the gap.

According to the invention, a partial oxidation of C3 and/or C4 precursor compounds to (meth)acrolein and/or (meth)acrylic acid is therefore carried out in a reactor which comprises thermoplate modules which are in turn formed from thermoplates, through which a heat carrier flows, absorbs the heat of reaction and thus at least partly evaporates. The thermoplate modules are configured with a cuboidal shape and are installed with pressure release in a predominantly cylindrical shell which completely surrounds them.

The thermoplate modules are formed from in each case two or more rectangular thermoplates which are arranged parallel to each other while in each case leaving a gap.

The thermoplates are manufactured from corrosion-free materials, preferably from stainless steel, for example having the materials number 1.4541 or 1.4404, 1.4571 or 1.4406, 1.4539 or else 1.4547, or from other alloyed steels.

The material thickness of the metal sheets used for this purpose may be selected between 1 and 4 mm, 1.5 and 3 mm, or else between 2 and 2.5 mm, or as 2.5 mm.

In general, two rectangular metal sheets may be joined at the longitudinal and end sides to give a thermoplate, in which case a roll seam or lateral weld joint or a combination of both is possible so that the space in which the heat carrier is later disposed is sealed on all sides. The edge of the thermoplates is advantageously removed at or even in the lateral roll seam of the longitudinal edge so that the edge region, which is poorly cooled if at all, and in which catalyst is usually also installed, has a very low geometric expansion.

The metal sheets are joined together by point welding distributed over the rectangular surface. An at least partial connection by straight or else curved and also circular roll seams is also possible. It is also possible for the volume flowed through by the heat carrier to be divided by additional roll seams into a plurality of separate regions.

One possibility of arranging the weld points on the thermoplates is in rows with equidistant point separations of from 30 to 80 mm or else from 35 to 70 mm, although separations of 40 to 60 mm are also possible and a further embodiment has separations of from 45 to 50 mm and also from 46 to 48 mm. Typically, as a result of the manufacture, the point separations vary by up to ±1 mm and the weld points of immediately adjacent rows, viewed in the longitudinal direction of the plates, are each arranged offset by half a weld point separation. The rows of the point welds in the longitudinal direction of the plates may equidistant with separations of from 5 to 50 mm, or else from 8 to 25 mm, although separations of from 10 to 20 mm and also from 12 to 14 mm, may also be used. Moreover, pairings of the weld point separations and row separations mentioned which are adapted to the application case are also possible. The row separations may be in a defined geometric relationship to the point separation, typically ¼ of the point separations or somewhat lower, so that there is a defined uniform expansion of the thermoplates in the course of the production. For predefined weld point and row separations, a corresponding number of weld points per $m^2$ of plate surface area is designated.

The breadth of the thermoplates is limited substantially by manufacturing technology considerations and may be between 100 and 2500 mm, or else between 500 and 1500 mm. The length of the thermoplates is dependent upon the reaction, in particular upon the temperature profile of the reaction, and may be between 500 and 7000 mm, or else between 3000 and 4000 mm.

In each case two or more thermoplates are arranged parallel and separated from one another to form a thermoplate module. This results in shaftlike gaps forming between immediately adjacent plates which, at the narrowest points of the plate separation, for example, have a width of between 8 and 150 mm, or else from 10 to 100 mm. One possible embodiment is also widths of from 12 to 50 mm or else from 14 to 25 mm, although from 16 to 20 mm may also be selected. A gap separation of 17 mm has also been tested.

Between the individual thermoplates of a thermoplate module, for example in the case of large-surface-area plates, spacers can additionally be installed in order to prevent deformations which can change plate separation or position. To install these spacers, sections of the metal plates can be removed from the flow region of the heat carrier, for example by circular roll seams, in order, for example, to be able to introduce holes into the plates for securing screws of the spacers.

The gaps may have the same separation, but, if required, the gaps may also be of different width when the reaction permits it or the desired reaction requires it, or apparatus or cooling technology advantages can be achieved.

The gaps of a thermoplate module filled with catalyst particles may be sealed with respect to each other, for example sealed by welding, or else be joined together on the process side.

To adjust the desired gap separation when joining the individual thermoplates together to form a module, the plates are secured in their position and in separation.

The weld points of immediately adjacent thermoplates may be opposite each other or offset from each other.

In general, preference is given for manufacturing reasons to configuring the arrangement with two or more cuboidal thermoplate modules with in each case identical dimensions. In the case of arrangements of 10 or 14 thermoplate modules, it may be advantageous for the compactness of the overall apparatus to select two module types having different edge length or different edge length ratios.

Preference is given to arrangements of 4, 7, 10 or 14 thermoplate modules having in each case identical dimensions. The projection surface of a module which is visible in the flow direction may be square, or else rectangular with a side ratio of 1.1 or else 1.2 Combinations of 7, 10 or 14 modules having rectangular module projections are advantageous, so that the diameter of the external cylindrical shell is minimized. Particularly advantageous geometric arrangements can be achieved when, as detailed above, a number of 4, 7 or 14 thermoplate modules is selected.

It should advantageously be possible in this connection to exchange the thermoplate modules individually, for example in the case of leaks, deformations of the thermoplates or in the case of problems which affect the catalyst.

Advantageously, the thermoplate modules are each arranged in a pressure-stable, rectangular stabilization frame.

Each thermoplate module is advantageously kept in position by a suitable guide, for example by the rectangular stabilization frames, with a laterally penetrating wall, or, for example, by an angle construction.

In one embodiment, the rectangular stabilization frames of adjacent thermoplate modules are sealed with respect to each other. This prevents bypass flow of the reaction mixture between the individual thermoplate modules.

The installation of cuboidal thermoplate modules into a predominantly cylindrical pressure-rated shell results in relatively large free intermediate spaces remaining at the edge toward the cylindrical jacket wall of the shell, in which accumulation, side reactions or decomposition of the material product can take place. Cleaning or decontamination of product, for example in the event of the necessity of assembly operations, is only possible there with great difficulty. It is therefore advantageous to separate this intermediate space from the reaction chamber, i.e. from the gaps between in each case immediately adjacent thermoplates.

To this end, the intermediate space between the thermoplate modules and the predominantly cylindrical shell is sealed at the lower end of the thermoplate module with a holding base. In order to prevent bypass flow of the reaction mixture, the bearing or holding base should seal the intermediate space gas-tight.

Advantageously, the intermediate space between the thermoplate modules and the predominantly cylindrical shell may also be sealed at the upper end of the thermoplate module by a metal sheet cover. However, a gas-tight seal is not necessary for this purpose; it is possible in one embodiment to configure the metal sheet cover with orifices.

The metal sheet cover at the upper end of the intermediate space between the thermoplate modules and the predominantly cylindrical shell may advantageously also be configured similarly to a valve tray.

The venting of the gas used to apply pressure may also be produced by means of an overflow unit, configured as a perforated plate, valve or force-loaded (for example with a spring or gas pressure), self regulating unit, also in combination with a blowback safeguard. These overflow units may also be disposed outside the cylindrical external shell.

The upper metal sheet cover may rest on struts which additionally stabilize the rectangular stabilization frames in which the thermoplate modules are installed.

The intermediate space between the thermoplate modules and the predominantly cylindrical shell may advantageously be filled with inert materials, in order to reduce the free gas volume there and in order to prevent gas convection which may lead, for example, to uncontrolled heat release.

In the cylindrical shell, it is advantageous to provide nozzles for the inlet and outlet of the inert bed material which are configured in suitable size and mounted at a suitable angle in such a way that blockage-free filling and emptying is possible under the force of gravity. Possible embodiments of the nozzles are nominal widths of 80, 100, 150 or 200 mm.

The inert material bed used may in principle be any chemically inert and sufficiently mechanically and thermally stable material, for example expanded perlite and/or expanded vermiculite.

It is possible to charge the intermediate space between the thermoplate modules and the predominantly cylindrical shell, which may be filled with inert material, with a gas pressure.

The application of pressure may be substantially constant and advantageously brought about by the pressure-regulated input and output of nitrogen. The regulation signal selected may be, for example, the pressure differential between the pressure in the intermediate space between the thermoplate modules and the predominantly cylindrical shell and the pressure at the lower end of the catalyst bed in the gaps of the thermoplate modules or at the upper end thereof. Advantageously, the differential pressure signal may be corrected by an offset value; a mean value, in particular the arithmetic mean value, of the pressure over the height of the catalyst bed may preferably be selected as the regulation signal.

To apply pressure, appropriate nozzles and/or an internal ring line having small drillholes, which are preferably directed downward, may be provided in the predominantly cylindrical shell.

Alternatively, it is also possible to bring about the application of pressure with continuous flow through the intermediate space with a gas which is inert or intrinsic to the process, in particular nitrogen or cycle gas.

The gas used to apply pressure is advantageously combined with the fluid reaction mixture at its outlet from the thermoplate modules, generally still within the predominantly cylindrical shell of the reactor. The outlet points of the gas used for pressure charging are advantageously located in flow dead zones of the fluid reaction mixture, in order to purge them.

The flow rate of the gas used to apply pressure will generally be significantly less than the flow rate of the fluid reaction gas mixture and is advantageously selected in such a way that it is not harmful to the reaction in process technology terms.

The thermoplate modules should advantageously each be individually exchangeable, in order that, as already outlined above, problems which occur, for example leakages, deformations of the thermoplates or problems with the catalysts, can be remedied in a targeted manner. For this purpose, it is advantageous to configure the thermoplate modules with some play with respect to the wall of the rectangular stabilization frames.

Since the thermoplate modules in this advantageous embodiment rest in the rectangular stabilization frames without sealing, bypass flows of the reaction medium may occur. In order to prevent this, the sites between the thermoplate modules and the rectangular stabilization frames where there is no seal are sealed in a suitable manner, for example with metal sheet strips which are mounted on the exterior of the thermoplate modules and press onto the wall of the rectangular stabilization frame when inserted into it. Alternatively, gas-tight metal sheet covers and connections, for example in the form of weld lip seals are possible.

Once the thermoplate modules have been inserted into the rectangular stabilization frames, they can be sealed with respect to the holding base, which seals the intermediate space between the thermoplate modules and the predominantly cylindrical shell at the lower end of the thermoplate modules. It is possible in principle to use any known sealing means for this purpose. These may be, for example, conventional seals which, for example, are additionally screw-secured.

It is also possible to bring about the sealing by weld lips, for example, by a variant in which a weld lip is secured to the holding base and a second weld lip to the outer edge of the thermoplate module or of the rectangular stabilization frame. Both weld lips are configured in such a way that they fit together geometrically and can be welded together. To exchange the thermoplate module, the weld seam is separated and, if required, renewed.

The thermoplate modules can be tensioned from above with the rectangular stabilization frames by a device. Sufficient tensile pressure from above ensures adequate surface pressure on the seal and advantageous securing of the thermoplate modules.

It is not obligatory for the rectangular stabilization frames to be sealed with respect to each other, as long as an impermissible bypass flow past the gaps is prevented. It is also possible to connect the rectangular stabilization frames together with small drillholes, through which the inert gas can flow in from the intermediate space and between thermoplate modules and the predominantly cylindrical shell, which prevents reactions in the space between the thermoplate module and the rectangular stabilization frame.

The thermoplate modules may additionally have guiding and directing elements on the exterior. It is possible, for example, to provide corner brackets of any form on the corners of these elements and conical metal sheet strips on their side. It is also advantageous to mount attachment devices or attachment auxiliaries on the modules, such as eyes, loops or threaded drillholes, in order to enable simple insertion by means of a hoist or, for example, of a crane. To insert the thermoplate modules by crane, they can also be held on tie bars which reach vertically through the initially empty gap down to the lower edge of the plates and are connected there to a transverse support to take up the load.

In a particular embodiment, the outermost thermoplate of a thermoplate module, at the exterior thereof, is formed from a thicker and therefore more stable metal sheet than the other metal sheets used to produce the thermoplates.

To compensate for the thermal expansion, annular compensators in particular are advantageously provided in or on the holding base which seals the intermediate space between the thermoplate modules and the predominantly cylindrical shell at the lower end of the thermoplate modules. Annular compensation with an approximately z-shaped profile viewed in the direction at right angles to the surface of the metal sheet base is particularly suitable. However, other conventional, wave-shaped compensators are equally suitable.

Preference is also given to also providing compensators for the axial and/or radial expansion in or on the metal metal sheet cover at the upper end of the intermediate space between thermoplate modules and predominantly cylindrical shell.

Each thermoplate module is supplied with the heat carrier by one or more distribution devices. The heat carrier, after flowing through the interior in the individual thermoplates, is removed at the other end of the thermoplate module via one or more collection devices. Since, in accordance with the invention, a heat carrier is used which absorbs the heat of reaction released and thus partly evaporates, it is particularly advantageous for the adjustment of the flow rates to provide in each case one distribution device, but two collection devices, per thermoplate module.

The distribution and collection devices are preferably configured in such a way that they each have a compensation for the accommodation of the thermal expansion of the thermoplate modules relative to the surrounding predominantly cylindrical shell. Compensation is possible here, for example, by a curved pipeline design.

To accommodate the thermal expansion of the thermoplate modules relative to the surrounding predominantly cylindrical shell, it is possible to ensure a suitable curved or Z- or omega-shaped geometric configuration of the tubing of the distribution and collection devices for the heat carrier flowing through the thermoplates. In a further embodiment, this compensation may be effected by axial or lateral compensators, in which case any pipe support required may be effected on an internal support structure.

Particular preference is given to configuring the collection tubes in the thermoplates for the feed and distribution, and also collection and removal, of the heat carrier by welding into a slotted tray as follows: the individual thermoplates of a module are initially joined to a channel-shaped metal sheet which is curved toward the interior of the thermoplates and has an approximately semicircular cross section and also orifices or slits for the output of the heat exchanger. At this stage of manufacture, it is possible to check that the weldings into the slotted tray are free of manufacturing faults, even in a representative specimen or else in the whole area, for example by X-ray. Subsequently, this first, approximately channel-shaped metal sheet is joined on both longitudinal sides to a second similarly shaped metal sheet, except having opposite curvature and no orifices or slots, in particular by longitudinal seam welding, to form a tubular component having virtually circular cross section. The two ends of this tubular component are sealed by lids which may optionally be strengthened by an internal tie rod.

In a further embodiment, it is also possible to directly weld tube parts having a relatively small nominal width of, for example, from 4 to 30 mm, onto the thermoplates, frequently onto the metal sheet edges, to feed and remove the heat carrier.

The gaps between the individual thermoplates of each thermoplate module serve to accommodate the heterogeneous particulate catalyst. At the upper side of the catalyst bed or at the upper end of the thermoplate modules, a cover, for example a perforated plate, can be mounted, which, when there is incident flow on the bed from below at a high flow rate, prevents loosening, fluidization or discharge of catalyst.

In order to rule out flow of the catalyst particles out of the gaps under the influence of gravity, catalyst grates have to be provided at the lower end thereof. This may be effected, for example, with perforated or mesh plates, and it is particularly advantageous for this purpose to use edge gap sieves, which ensure good retention of the catalyst with simultaneously high dimensional stability and low pressure drop for the reaction medium flowing through.

The catalyst retention grates may be installed, for example, in such a way that they can be swiveled.

It is particularly advantageous when the distribution devices for the heat carrier to the thermoplates are installed in such a way that the lateral separations from the distribution devices to the edge of the thermoplate assembly are the same, so that only a single type of catalyst-retaining grate is required. In each case two catalyst-retaining grates are provided per thermoplate module, i.e. on both sides of the distribution device for the heat carrier.

The catalyst-retaining grates are advantageously dimensioned in such a way that they can installed and deinstalled via the manholes in the predominantly cylindrical shell. The manholes frequently have an internal diameter of 700 mm.

Correspondingly, preference is given to an edge length for the catalyst inlay grates of 650 mm.

In a further embodiment, it is possible to further divide these retaining grates into smaller units, but also to individually seal each gap or each gap half individually, so that it can also be emptied separately.

Alternatively, it is also possible to fill the thermoplate modules with catalyst before they are installed into the reactor, i.e. outside the reactor.

The shell surrounding the thermoplate modules has been described above as predominantly cylindrical. In this context, this means that it has a cylindrical jacket with circular cross section which is sealed at both ends in each case by a hood.

The predominantly cylindrical shell is generally installed vertically.

The fluid reaction medium is passed into the reactor interior via one hood, frequently via the lower hood, flows through the gap which is filled with the heterogeneous particulate catalyst and is between the individual thermoplates, and is removed at the other end of the reactor, via the other, frequently the upper, hood.

The hoods are preferably manufactured from stainless steel or are stainless steel-plated.

The hoods may be connected to the cylinder jacket of the shell by secure welding or separably, for example via a flanged connection. The flange connection may be configured in such a way that it can be lowered by means of a hydraulic system.

It is advantageously possible to reach the circumference of the hoods on foot via one of more manholes which generally have a diameter of 700 mm. For this purpose, a widened cylindrical section is advantageous, which, like the hood, is, for example, manufactured from stainless steel or is stainless steel-plated.

It is possible via the manholes in the hoods to access the upper side of the modules, so that the catalyst can be introduced into the gaps between the thermoplates, and to the lower side of the modules, so that the retaining grids can be installed and deinstalled easily.

To deinstall the catalyst, devices may additionally be installed in the lower hood to retain auxiliaries and to collect the catalyst, which may have already been installed in the course of operation, and also one or more nozzles to discharge the catalyst.

The material used for the intermediate space between the thermoplate modules and the interior wall of the predominantly cylindrical shell sealing holding base, and for the rectangular stabilization frames for the thermoplate modules too, may be carbon steel. Alternatively, it is possible to use stainless steel for this purpose.

In one or both hoods, it is advantageous to install nozzles, through which multithermoelements can be introduced into the individual thermoplate modules. In addition, nozzles may be mounted there for further field instruments and process analytical devices.

Preference is given to providing, in the cylindrical jacket of the predominantly cylindrical shell, one or more compensators to accommodate preferably the axial thermal expansion.

The invention provides the use of a reactor for carrying out partial oxidations of a fluid reaction mixture, in which the heat of reaction is removed by a heat carrier flowing through the thermoplates which thus at least partly evaporates.

The reactor in the strongly exothermic reactions is operated, for example, in such a way that the fluid reaction mixture is fed via the lower hood and removed from the reactor via the upper hood.

Since the heat carrier medium, which removes the heat of reaction in particular by evaporative cooling, is passed from below into the thermoplates, when the reaction mixture is fed from below, i.e. when there is cocurrent flow of reaction mixture and heat carrier, sufficient heat carrier is always available.

In addition, both in terms of construction and the flow control of the reaction medium and the operation, it has to be ensured that neither is the reaction medium excessively cooled by supercooled heat carrier before it reaches the active catalyst zone, nor is the heat carrier pre-evaporated to an impermissibly high degree.

The heat carrier medium used may be feed water as typically utilized in power stations for steam generation and corresponding to the prior art (Technische Regeln für Dampfkessel [Technical rules for vapor vessels] (TRD) 611 of Oct. 15, 1996 in BArbBl. December/1996 p. 84, last altered on Jun. 25, 2001 in BArbBl. August/2001 p. 108). Typical parameters of the feed water may be: conductivity less than 0.4, or less than 0.2, microsiemens/cm, calcium and magnesium hardness less than 0.005 millimole per liter or below the detection limit, sodium less than 5 micrograms per liter, silicon dioxide less than 20 micrograms per liter, iron less than 50 micrograms per liter and oxygen less than 20 micrograms per liter, and a total content of dissolved carbon of less than 0.2 milligram per liter. In addition, the feed water should be low in or free of halogen, in particular chlorine. It is also possible to condition the feed water in a targeted manner, for example by adding auxiliaries such as hydrazine, ammonia, and in particular to make it alkaline; in addition, corrosion inhibitors can be added to the feed water.

The upper hood, through which the reaction medium leaves the reactor in the above-described preferred process control, may consist of carbon steel.

In order to ensure access to the thermal plate modules for the purpose of repair or exchange, it likewise has to be possible to remove the upper hood. When there is no flange connection, the upper hood can be removed and welded on again after module assembly.

It is possible to integrate the steam removed from the thermoplates into different steam rails.

The reactor may optionally be attached to two steam rails, one of which has a higher pressure and is utilized for the heating of the reactor to operating temperature.

It is advantageous to operate on only one steam rail.

The reactor can preferably be operated with natural circulation of the cooling medium, water, and a ratio of feed water to steam of generally from 3 to 12, preferably from 5 to 10.

It is possible to operate with forced circulation, in which case a wider load variation of the cooling is possible. To this end, the feed water is fed at a higher pressure than present in the cooling system, for example by means of a pump.

The feed water circulation rate in the distribution devices may be set between 0.5 and 3.0 m/s, or else from 1.0 to 2.0 m/s, and the water circulation number between 3 and 12. The flow rate of the biphasic flow (steam/water) in the collection devices may be between 0.5 and 15 m/s, or else between 2.0 and 6.0 m/s.

Particular preference is given to carrying out the heating of the thermoplate modules to start up the reactor from the same heat carrier network into which the heat is removed at by least partly evaporated heat carrier medium in the course of reaction operation.

The regulation of the steam pressure in the cooling system makes it possible to precisely adjust the cooling temperature. Experience has shown that the thermoplates can be operated up to a pressure of about 80 bar in the coolant. The reactor according to the invention enables direct steam generation at pressure levels up to 80 bar.

The reactor can be used to carry out the partial oxidations according to the invention on the industrial scale.

Compared to the filling of a large number, frequently a five-figure number, of catalyst tubes, the provision of the catalyst and the filling with catalyst of a two- or three-figure number of gaps between the thermoplates at equal product capacity with catalyst is associated with distinctly reduced cost and inconvenience.

The modular configuration allows the reactor to be adapted flexibly to the required capacity. A relatively small number of thermoplate modules may be installed or operated in comparison to the maximum possible number restricted by the relative geometry of the shell and of the thermoplate modules. It is also possible when required to isolate individual modules from process gas flow and to operate the reaction with reduced capacity under the same external conditions.

It is possible to deliver the reactor in individual parts and assemble it at the use location.

The invention is illustrated in detail hereinbelow with the aid of drawings.

Figure 1:
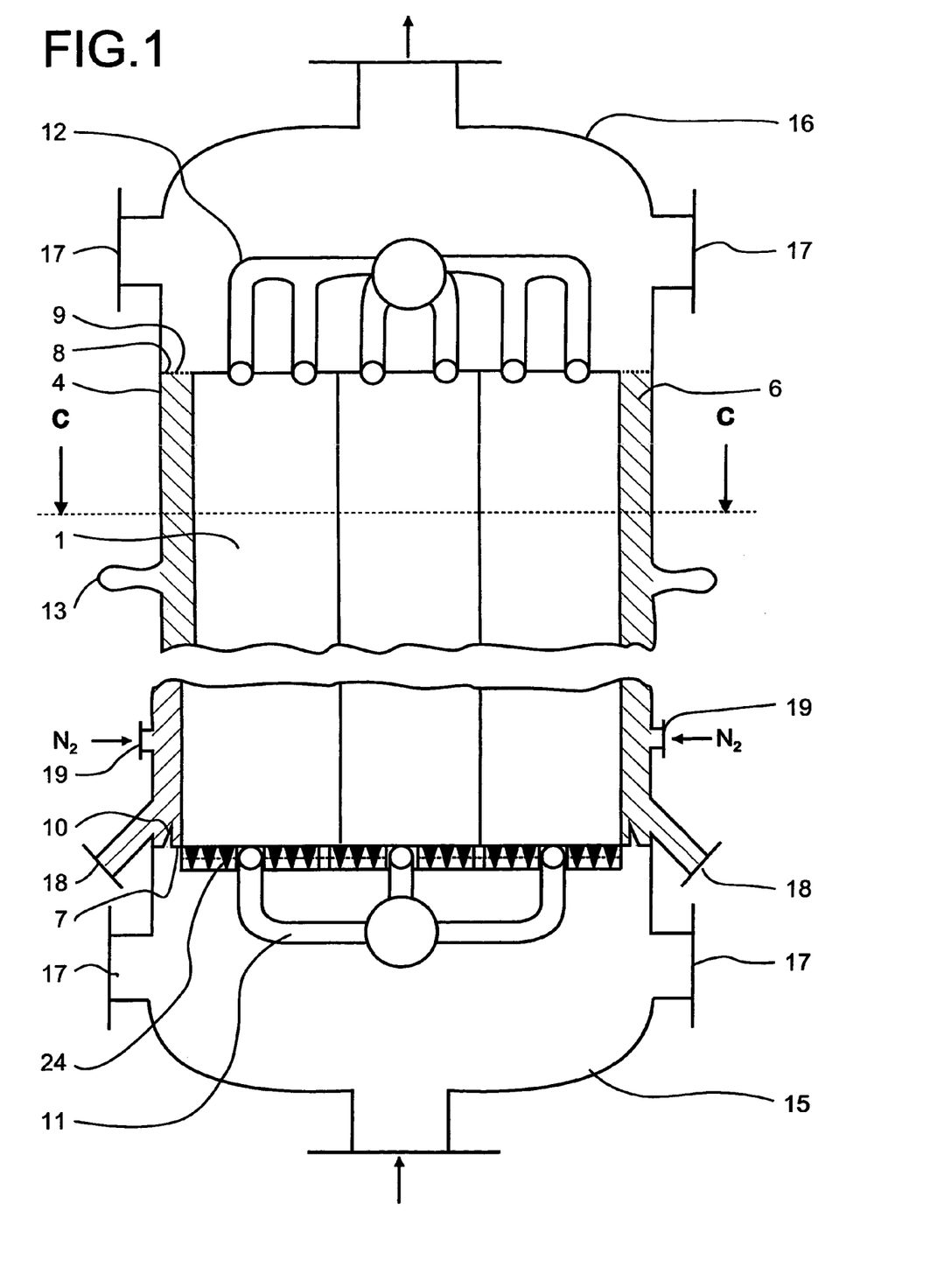
FIG. 1 shows a longitudinal section through a preferred embodiment of a reactor according to the invention with the cross section C-C in FIG. 1A, and also further preferred arrangements of thermoplate modules in cross section in FIGS. 1B to 1F.

The longitudinal section illustration through a preferred embodiment in FIG. 1 shows a reactor having thermoplate modules 1 which are surrounded by a predominantly cylindrical shell 4. The intermediate space 6 between the thermoplate modules 1 and the predominantly cylindrical shell 4 is sealed gas-tight in the region of the lower end of the thermoplate module 1 by a holding base 7, and, in the region of the upper end of the thermoplate modules 1, by a sheet metal cover 8 which, preferred embodiment illustrated in the figure, has orifices 9.

At the lower end of the thermoplate modules 1 is provided a distribution device 11 for the heat carrier, frequently feed water, and, in the region of the upper end of the thermoplate modules 1, a collection device 12 for the heat carrier, which is frequently present in this region as steam or as a water/steam mixture. The predominantly cylindrical shell 4 has compensators 13 for the thermal expansion.

In the preferred embodiment illustrated in FIG. 1, the fluid reaction medium is fed via the lower hood 15 and removed via the upper hood 16. In the region of the lower hood 15, and also in the region of the upper hood 16, is disposed in each case an additional cylindrical section with in each case two manholes 17. In the predominantly cylindrical shell 4 are provided nozzles 18 for the emptying of the inert material from the intermediate space 6 between the thermoplate modules 1 and the predominantly cylindrical shell 4, and also nozzles 19 for the feeding of nitrogen into the intermediate space 6. The catalyst is retained by catalyst grates 24 which are configured, for example, as edge gap sieves.

Figure 1A:
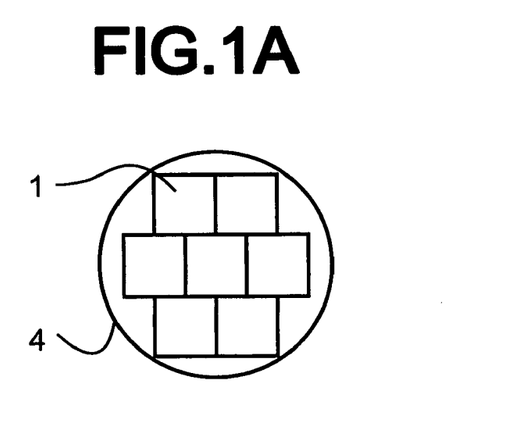

The cross-sectional illustration in the plane C-C in FIG. 1A shows a preferred arrangement of advantageously seven thermoplate modules 1 with intermediate space 6 between the thermoplate modules 1 and the shell 4, which is preferably filled with inert material.

Figure 1B:
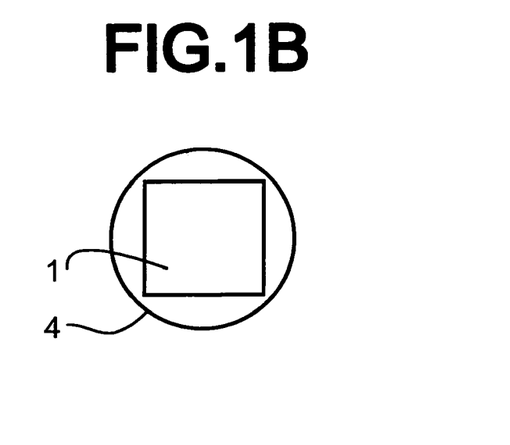

FIG. 1B shows a cross-sectional illustration having a single thermoplate module with square cross section which is arranged in the shell 4.

Figure 1C:
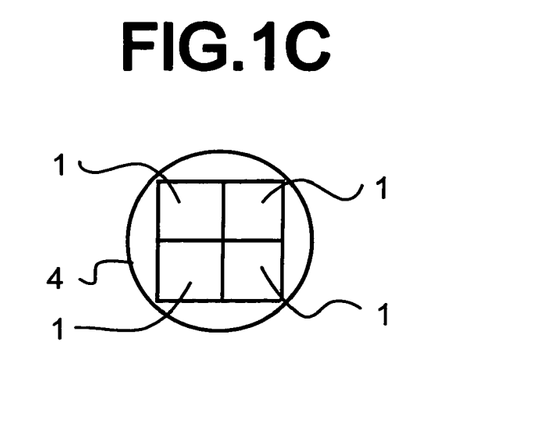

FIG. 1C shows an embodiment with four thermoplate modules 1 having a square cross section in the shell 4.

Figure 1D:
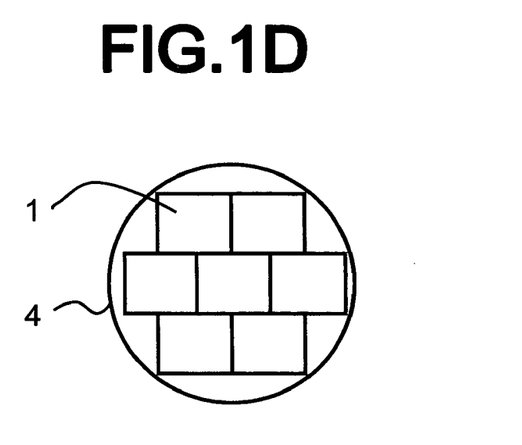

FIG. 1D shows an embodiment with seven thermoplate modules having a rectangular cross section and a side ratio of in each case 1:1.2.

Figure 1E:
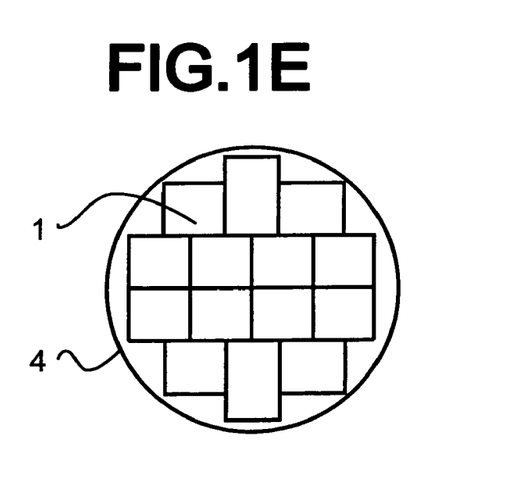

FIG. 1E shows an embodiment with eleven thermoplate modules having a rectangular cross section and a side ratio of in each case 1:1.1.

Figure 1F:
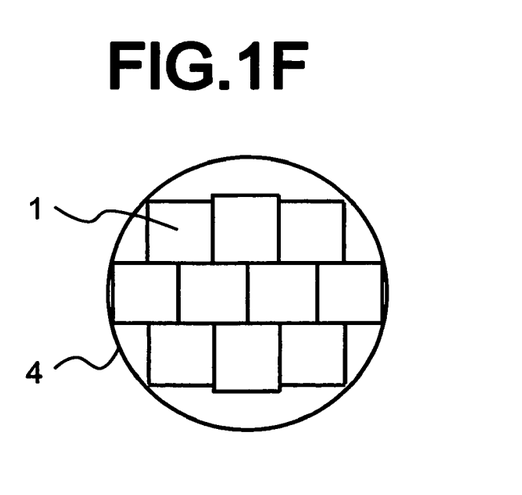

FIG. 1F shows an embodiment with ten thermoplate modules 1 with in each case rectangular cross section and a side ratio of in each case 1:1.1.

Figure 2:
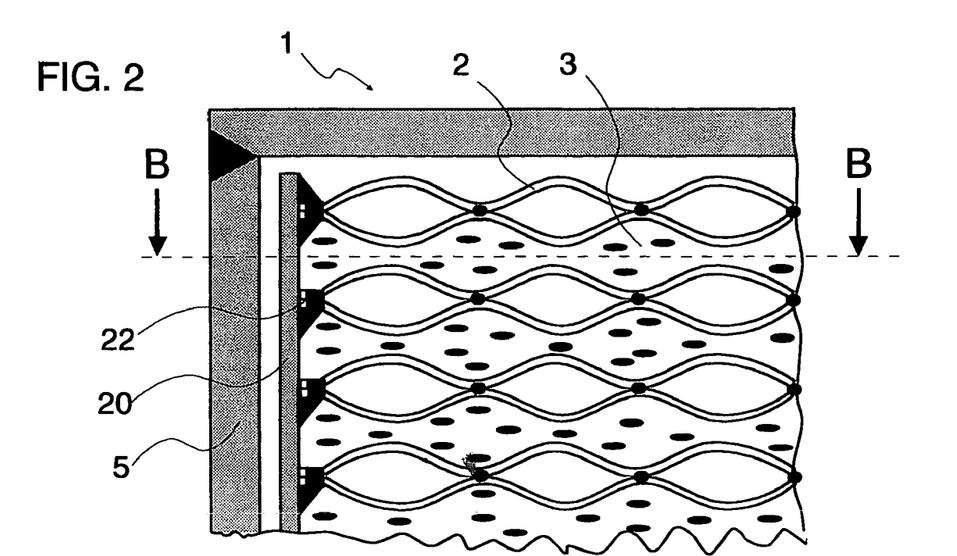
FIG. 2 shows a detailed illustration of a thermoplate module in cross section to the thermoplates, with longitudinal section illustrations in the planes A-A and B-B in FIGS. 2A and 2B respectively.

FIG. 2 illustrates a section of a thermoplate module 1 with thermoplates 2 and gaps 3 between the thermoplates to accommodate the heterogeneous particulate catalyst. The figure illustrates the weld points between the metal sheets forming the individual thermoplates 2, and also the securing of the thermoplates 2 at their lateral edges in a lateral boundary 20. The thermoplate module is inserted into a rectangular stabilization frame 5.

Figure 2A:
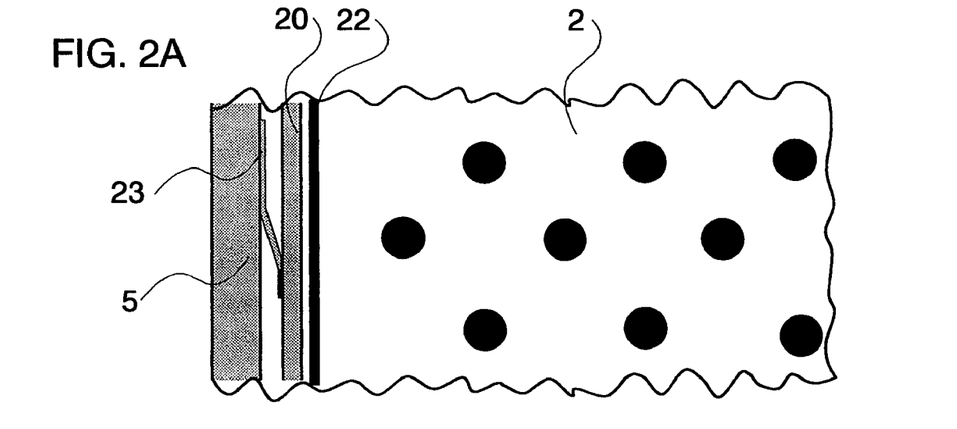

The sectional illustration in the plane A-A in FIG. 2A illustrates the lateral roll seam weld 22 which seals the individual thermoplates, and also the sealing strips 23 between the thermoplates 2 of the thermoplate module 1 and the wall of the rectangular stabilization frame 5. The figure also shows a preferred arrangement of the weld points on the thermoplates 2.

Figure 2B:
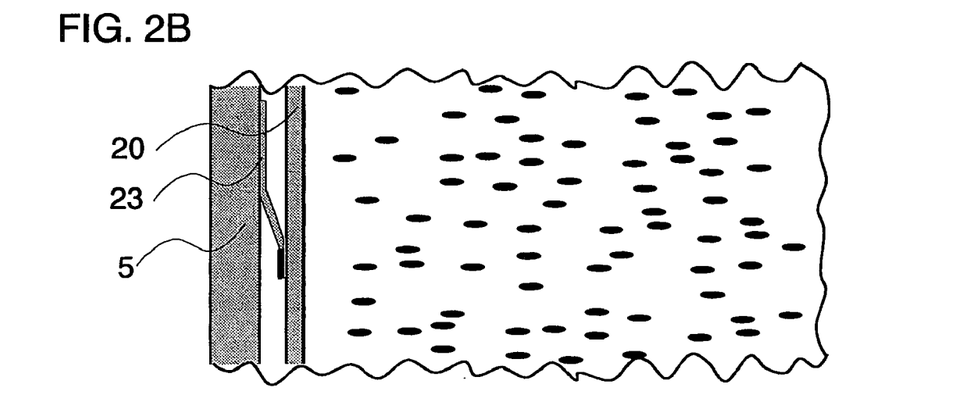

The section B-B which is shown in FIG. 2B is located in a plane through the gap 3 filled with the particulate catalyst. Between the lateral boundary 20 of the thermoplate module 1 and the wall of the rectangular stabilization frame 5 are provided sealing strips 23.

Figure 3:
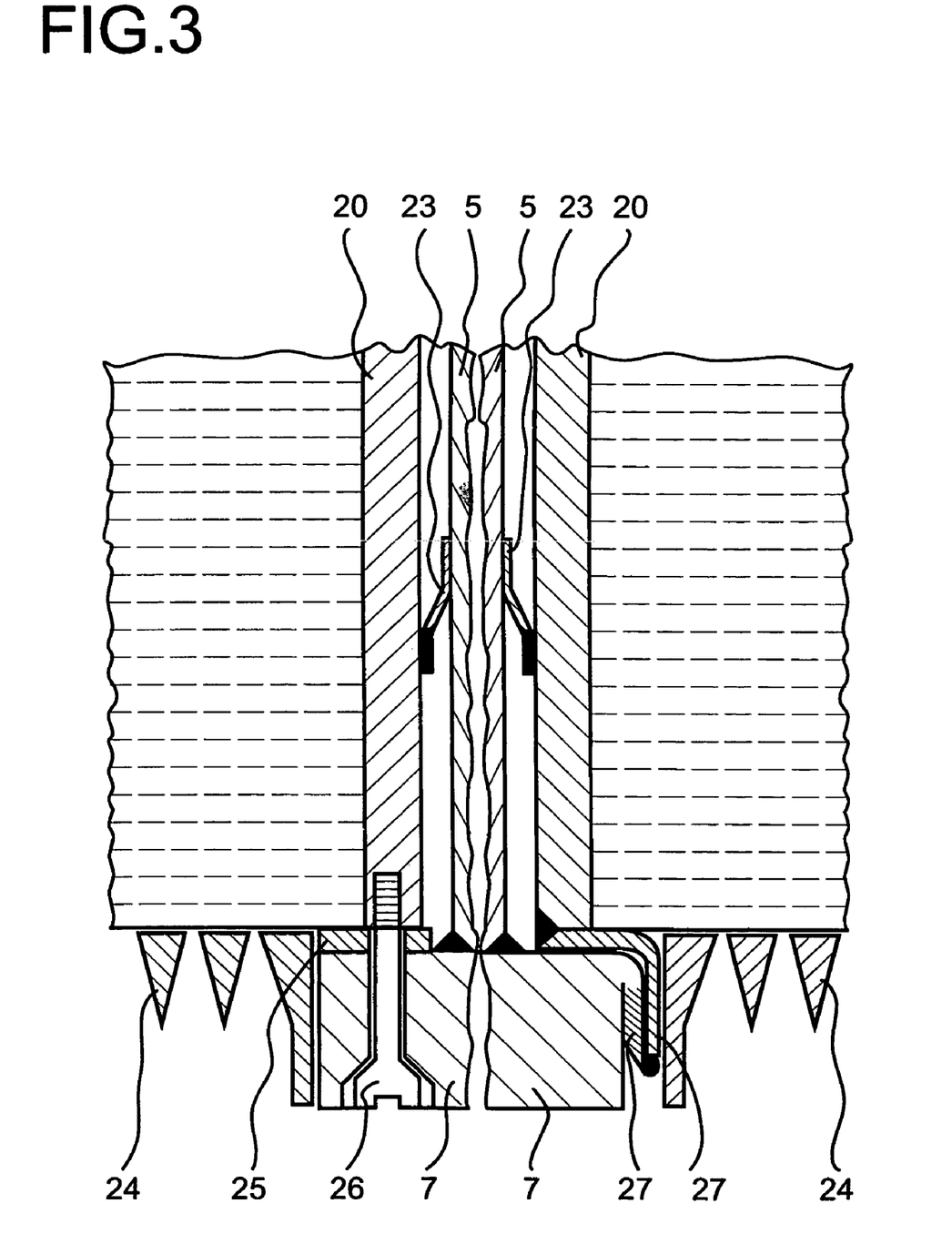
FIG. 3 shows two possible embodiments of seals between holding base and stabilization cases.

FIG. 3 shows two different variants for sealing the thermoplate modules with respect to the holding base. The left-hand side of the diagram shows a seal 25 between the holding base 7 and the lateral boundary 20 of a thermoplate module, and the connection is secured by a screw 26. The detail also shows a section of the edge gap sieve 24 used as a catalyst grate, and also a sealing strip 23 between the lateral boundary 20 of the thermoplate module and the rectangular stabilization frame 5.

The right-hand side of the diagram in FIG. 3 shows a further variant of a seal between holding base 7 and thermoplate module, specifically by means of two weld lips 27, one of which is welded to the holding base 7 and the second to the lateral boundary 20 of the thermoplate module. The two weld lips are subsequently joined together with a weld seam.

Figure 4:
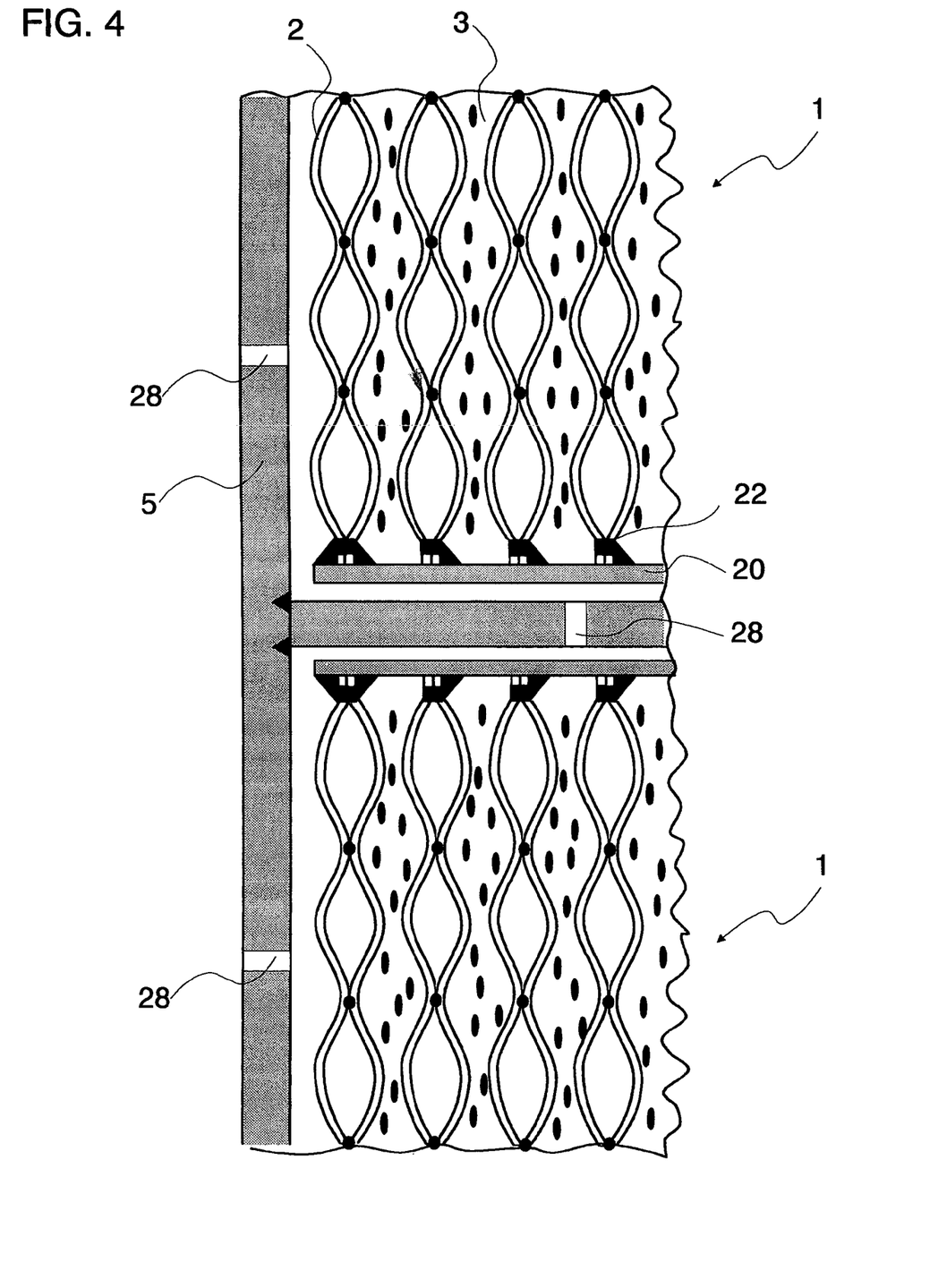
FIG. 4 shows a detailed illustration with drillholes in the rectangular stabilization frames.

FIG. 4 shows an embodiment with drillholes 28 in the rectangular stabilization frames 5, which allows gas used to apply pressure to flow from the intermediate space between the thermoplate modules and the shell into the spaces between the thermoplate modules 1 and the rectangular stabilization frames 5.

Figure 5A:
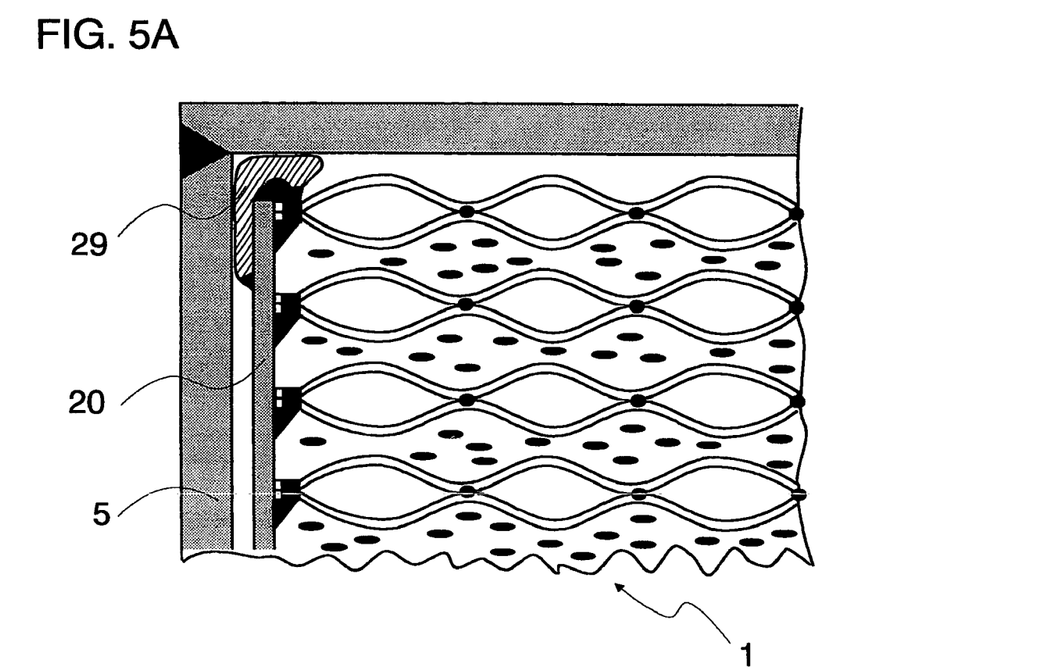
FIGS. 5A, 5B and 5D to 5I show detailed illustrations with additional guiding and directing elements on the exteriors of the thermoplate module.

FIG. 5A shows an in detailed illustration of a corner bracket 29 on the exterior of the lateral boundary 20 of a thermoplate module 1 for conducting and directing with respect to the rectangular stabilization frame 5.

Figure 5B:
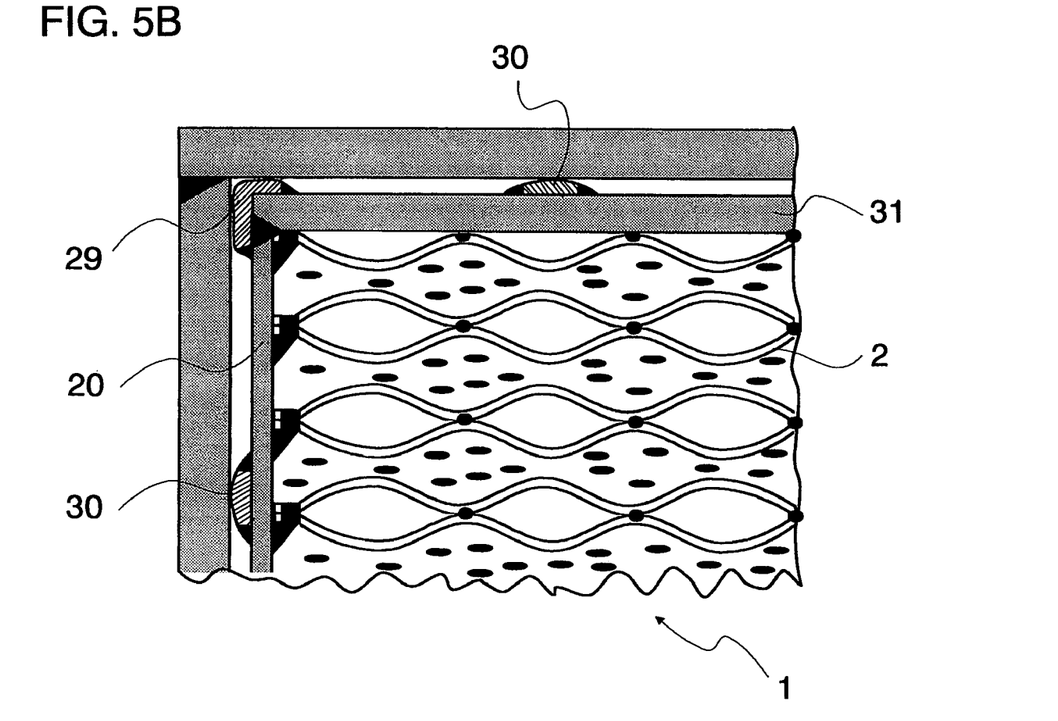

The detailed illustration in FIG. 5B shows, in addition to the corner bracket 29, conical metal sheet strips 30 on the side of the thermoplate modules 1 as guiding and directing elements.

In addition, FIG. 5B shows a possible embodiment for the outermost thermo plate 2 in the thermoplate module 1, and specifically the outer metal sheet of the outermost thermoplate 2 of the thermoplate module 1 is thicker and thus more stable compared to the remaining metal sheets forming the thermoplates 2.

Figure 5D:
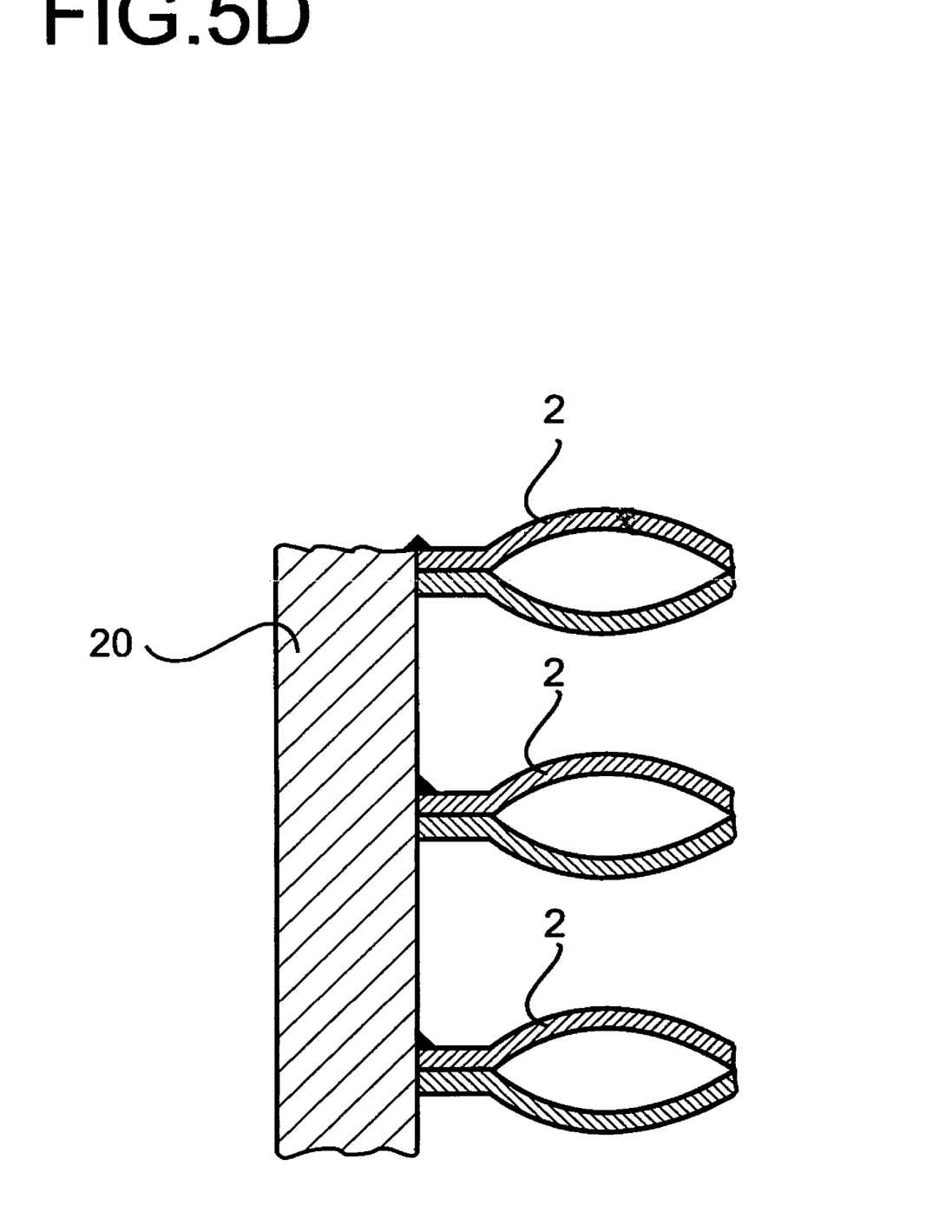
Figure 5E:
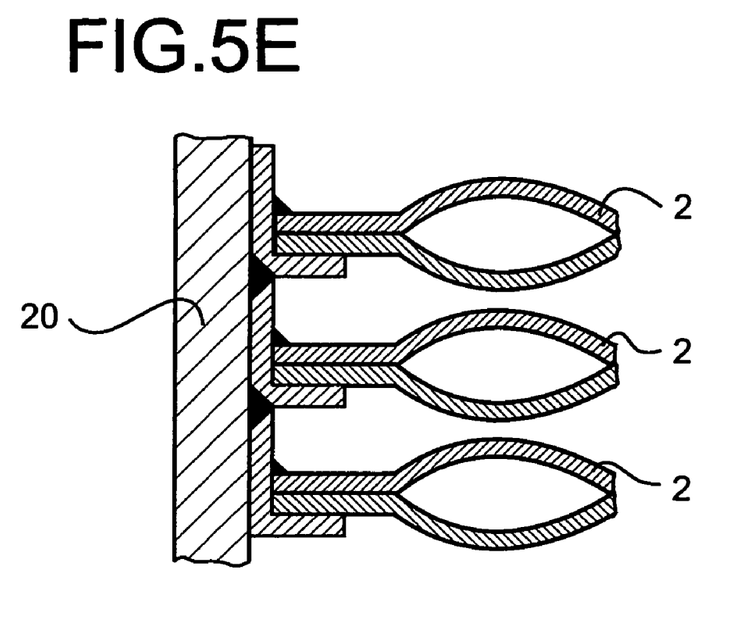
Figure 5F:
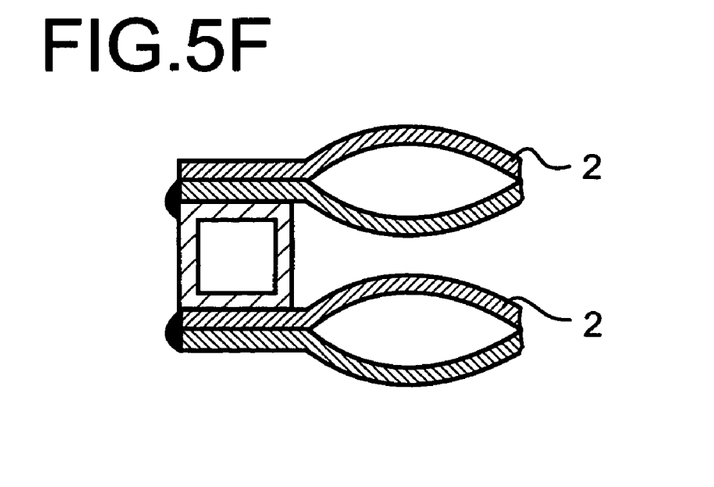
Figure 5G:
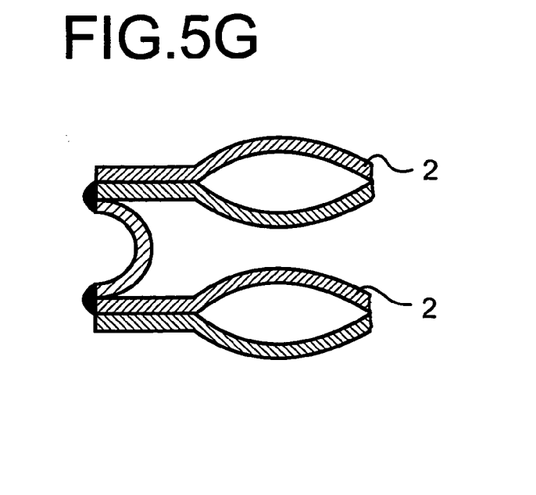
Figure 5H:
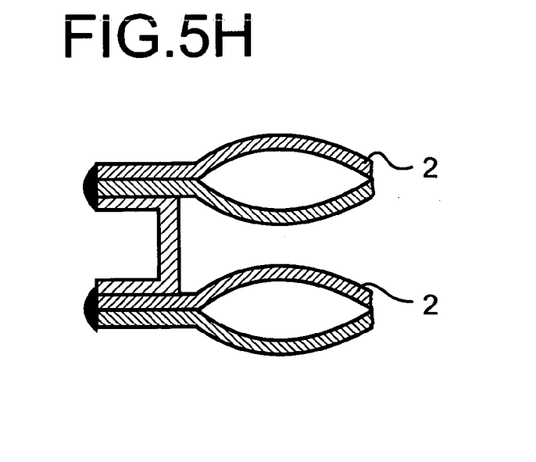
Figure 5I:
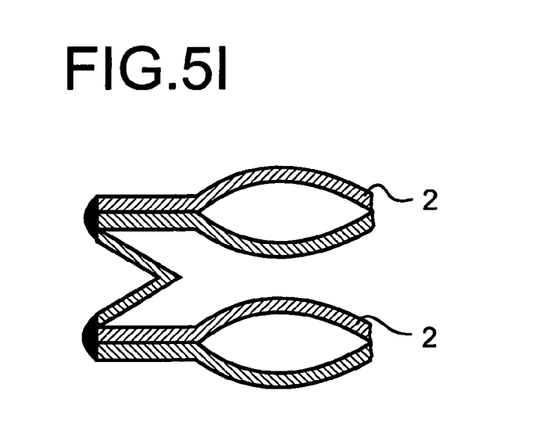

FIGS. 5D to 5I show schematics of different variants for securing the thermoplates 2 to the lateral boundary 20:
in the embodiment in FIG. 5D, the thermoplates 2 are welded on;
in FIG. 5E, two angles welded onto the lateral boundary 20 are provided to secure the thermoplates;
in the embodiment in FIG. 5F, square tubes;
in the embodiment in FIG. 5G, half tubes,
in the embodiment in FIG. 5H, U-profiles; and
in FIG. 5I, angled profiles.

Figure 6:
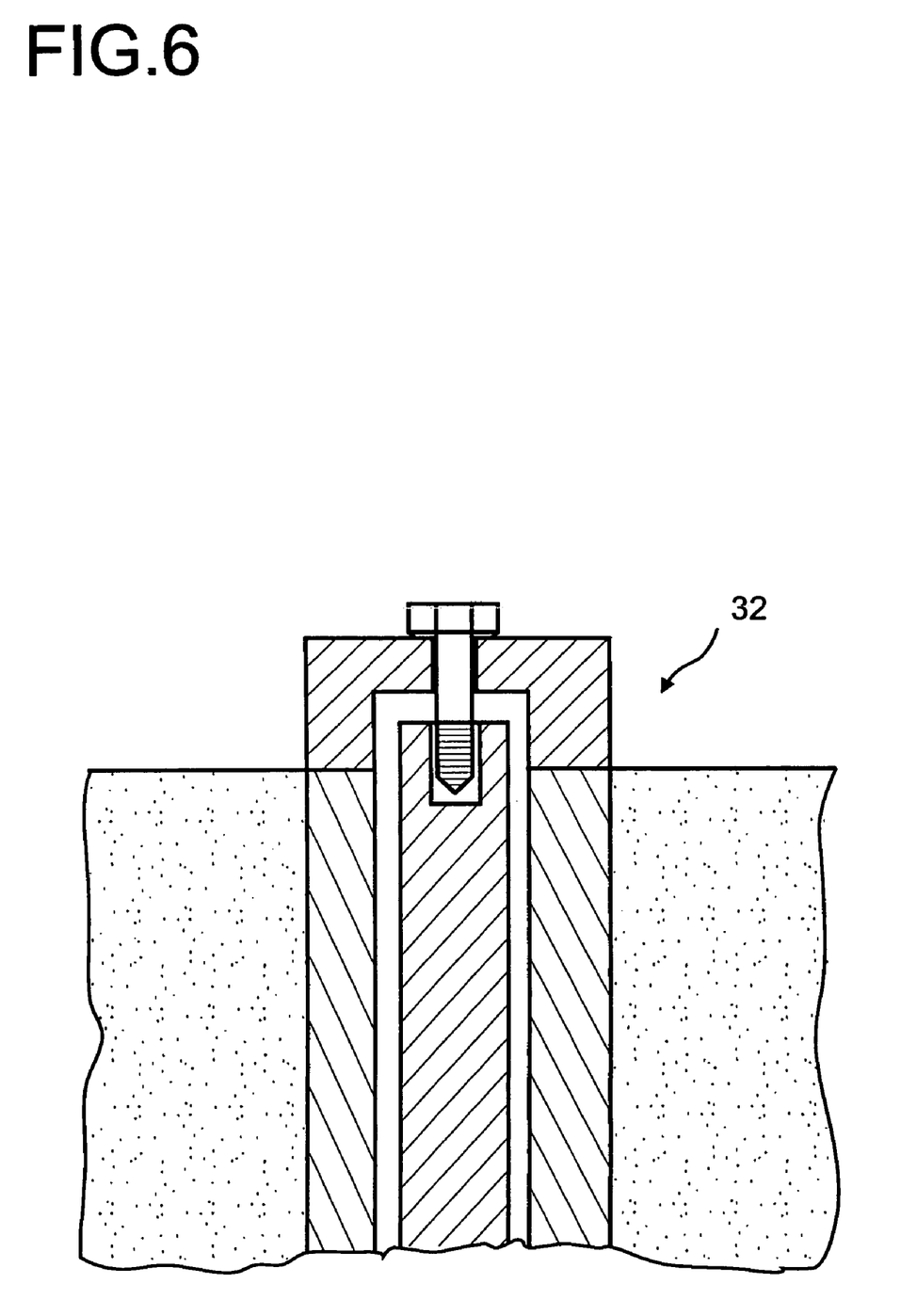
FIG. 6 shows a detailed illustration of a tension device for securing the thermoplate modules in the rectangular stabilization frames.

FIG. 6 shows a schematic of a tension device 32 for tensioning between thermoplate modules and the rectangular stabilization frames 5.

We claim:

1. A process for partial oxidation in the gas phase of C3 and/or C4 precursor compounds to (meth)acrolein and/or (meth)acrylic acid in the presence of a heterogeneous particulate catalyst in a reactor comprising
    one or more cuboidal thermoplate modules which are each formed from two or more rectangular thermoplates arranged parallel to each other while in each case leaving a gap which can be filled with the heterogeneous particulate catalyst and is flowed through by a fluid reaction mixture, the heat of reaction being absorbed by a heat carrier which flows through the thermoplates and thus at least partly evaporating, and also comprising
    a predominantly cylindrical shell which releases the pressure at the thermoplate modules, completely surrounds them and comprises a cylinder jacket and hoods which seal it at both ends and whose longitudinal axis is aligned parallel to the plane of the thermoplates, and also comprising
    one or more sealing elements which are arranged in such a way that the fluid reaction mixture, apart from flowing through the reactor interior spaces bounded by the hoods, only flows through the gap(s).

2. A process as claimed in claim 1, wherein the reactor has two or more cuboidal thermoplate modules each having the same dimensions.

3. A process as claimed in claim 2, wherein the reactor comprises 4, 7, 10 or 14 thermoplate modules.

4. A process as claimed in claim 1, wherein the thermoplates are formed from in each case two rectangular metal sheets which are joined at their longitudinal and end sides by roll seam welding, and the edge of the metal sheets protruding outward over the roll seam is removed at the outer edge of the roll seam or in the roll seam itself.

5. A process as claimed in claim 1, wherein the thermoplate modules are in each case arranged in a pressure-stable rectangular stabilization frame.

6. A process as claimed in claim 5, wherein the rectangular stabilization frames of adjacent thermoplate modules are welded and sealed together.

7. A process as claimed in claim 1, wherein the sealing element provided is a holding base which seals the intermediate space between the thermoplate modules and the predominantly cylindrical shell at the lower ends of the thermoplate modules.

8. A process as claimed in claim 7, wherein a metal sheet cover seals the intermediate space between the thermoplate modules and the predominantly cylindrical shell at the upper end of the thermoplate modules.

9. A process as claimed in claim 8, wherein the metal metal sheet cover has orifices.

10. A process as claimed in claim 1, wherein the intermediate space between the thermoplate modules of the shell is filled with an inert material.

11. A process as claimed in claim 10, wherein the inert material is expanded perlite and/or expanded vermiculite.

12. A process as claimed in claim 1, wherein pressure is applied to the intermediate space between the thermoplate modules and the predominantly cylindrical shell with a gas.

13. A process as claimed in claim 12, wherein the pressure applied is substantially constant.

14. A process as claimed in claim 13, wherein the substantially constant application of pressure is effected by pressure-regulated feed and removal of nitrogen.

15. A process as claimed in claim 12, wherein the pressure is applied by continuously feeding a gas which is inert or intrinsic to the process, in particular nitrogen or cycle gas, through the intermediate space.

16. A process as claimed in claim 15, wherein the gas used to apply pressure is combined with the fluid reaction mixture at its outlet from the thermoplate modules.

17. A process as claimed in claim 1, wherein compensators for the radial expansion are provided in or on the holding base.

18. A process as claimed in claim 1, wherein compensators for the axial and/or radial expansion are provided in or on the metal metal sheet cover.

19. A process as claimed in claim 1, wherein one or more distribution devices and one or more collection devices for the heat carrier are used per thermoplate module.

20. A process as claimed in claims 1, wherein one distribution device and two collection devices for the heat carrier are used per thermoplate module.

21. A process as claimed in claim 1, wherein the distribution and collection devices for the heat carrier have uniform dimensions.

22. A process as claimed in claim 1, wherein the distribution devices and collection devices for the heat carrier are welded into a slotted base.

23. A process as claimed in claim 1, wherein distribution devices and collection devices for the heat carrier flowing through the thermoplates are provided which each have compensation for the accommodation of the thermal expansion of the thermoplate modules relative to the surrounding, predominantly cylindrical shell.

24. A process as claimed in claim 1, wherein the thermal expansion of the thermoplate modules relative to the surrounding, predominantly cylindrical shell is accommodated by suitable curved geometric design of the tubing of the distribution devices and collection devices for the heat carrier flowing through the thermoplates.

25. A process as claimed in claim 1, wherein two catalyst holding grates per thermoplate module are used.

26. A process as claimed in claim 1, wherein the catalyst holding grates can be introduced into the reactor jacket through the manholes present in the reactor.

27. A process as claimed in claim 1, wherein one or more compensators for accommodating thermal expansion are provided in the cylinder jacket of the predominantly cylindrical shell.

28. A process as claimed in claim 1, wherein the heat of reaction is removed by a heat carrier flowing through the thermoplates which is thus at least partly evaporated.

29. A process as claimed in claim 27, wherein the thermoplate modules are heated by the same heat carrier flowing through the thermoplates into which the heat is removed in the course of reaction operation by an at least partially evaporated heat carrier medium.

30. A process as claimed in claim 27, wherein the thermal expansion is axial thermal expansion and one or more compensators for accommodating the axial thermal expansion are provided in the cylinder jacket of the predominantly cylindrical shell.

* * * * *

UNITED STATES PATENT AND TRADEMARK OFFICE
CERTIFICATE OF CORRECTION

PATENT NO. : 7,268,254 B2 Page 1 of 1
APPLICATION NO. : 10/889081
DATED : September 11, 2007
INVENTOR(S) : Olbert et al.

It is certified that error appears in the above-identified patent and that said Letters Patent is hereby corrected as shown below:

On the title page, Item (75), the Inventors information is incorrect. Item (75) should read:

-- (75) Inventors: Gerhard Olbert, Dossenheim (DE);
Claus Hechler, Ludwigshafen (DE) --

Signed and Sealed this

Twentieth Day of November, 2007

JON W. DUDAS
*Director of the United States Patent and Trademark Office*